Figure 1:
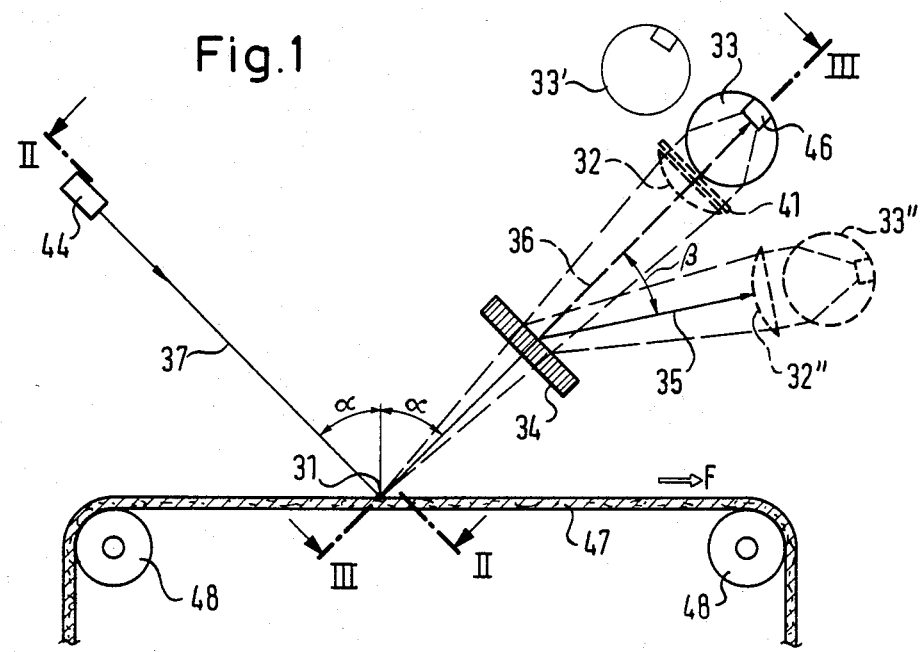

United States Patent [19]

Röss et al.

[11] Patent Number: 4,532,430

[45] Date of Patent: Jul. 30, 1985

[54] FAULT DETECTION APPARATUS FOR MATERIAL WEBS

[75] Inventors: Dieter Röss, Planegg; Klaus Ostertag, Munich, both of Fed. Rep. of Germany

[73] Assignee: Erwin Sick GmbH Optik-Elektronik, Waldkirch, Fed. Rep. of Germany

[21] Appl. No.: 563,602

[22] Filed: Dec. 20, 1983

Related U.S. Application Data

[62] Division of Ser. No. 235,694, Feb. 18, 1981, Pat. No. 4,450,359.

[30] Foreign Application Priority Data

Feb. 19, 1980 [DE] Fed. Rep. of Germany ....... 3006072

[51] Int. Cl.$^3$ ............................................. G01N 21/88
[52] U.S. Cl. .................................... 250/572; 250/227
[58] Field of Search ............... 250/227, 559, 562, 563, 250/571, 572; 356/429, 430, 431, 443, 444; 350/96.24, 96.28

[56] References Cited

U.S. PATENT DOCUMENTS

| | | | |
|---|---|---|---|
| 4,181,398 | 1/1980 | Sick | 250/227 |
| 4,295,743 | 10/1981 | Sick | 356/431 |
| 4,306,813 | 12/1981 | Sick | 250/572 |

Primary Examiner—David C. Nelms

[57] ABSTRACT

Faults in a material web are detected by scanning the web with a beam of light along a line transverse to its direction of movement and by detecting the angular ranges into which the incident light is scattered by these faults. For this purpose a light conducting rod is arranged parallel to the scanned line in a reception plane. The light conducting rod has a stepped prism arrangement along its side surface opposite to the light inlet and the inclination of the individual, unmirrored, prism surfaces is such that specularly reflected light passes through the prisms whereas scattered light falls on the prism surfaces at angles of total reflection and is reflected to a photodetector at an end face of the light conducting rod.

2 Claims, 14 Drawing Figures

U.S. Patent    Jul. 30, 1985    Sheet 1 of 9    4,532,430

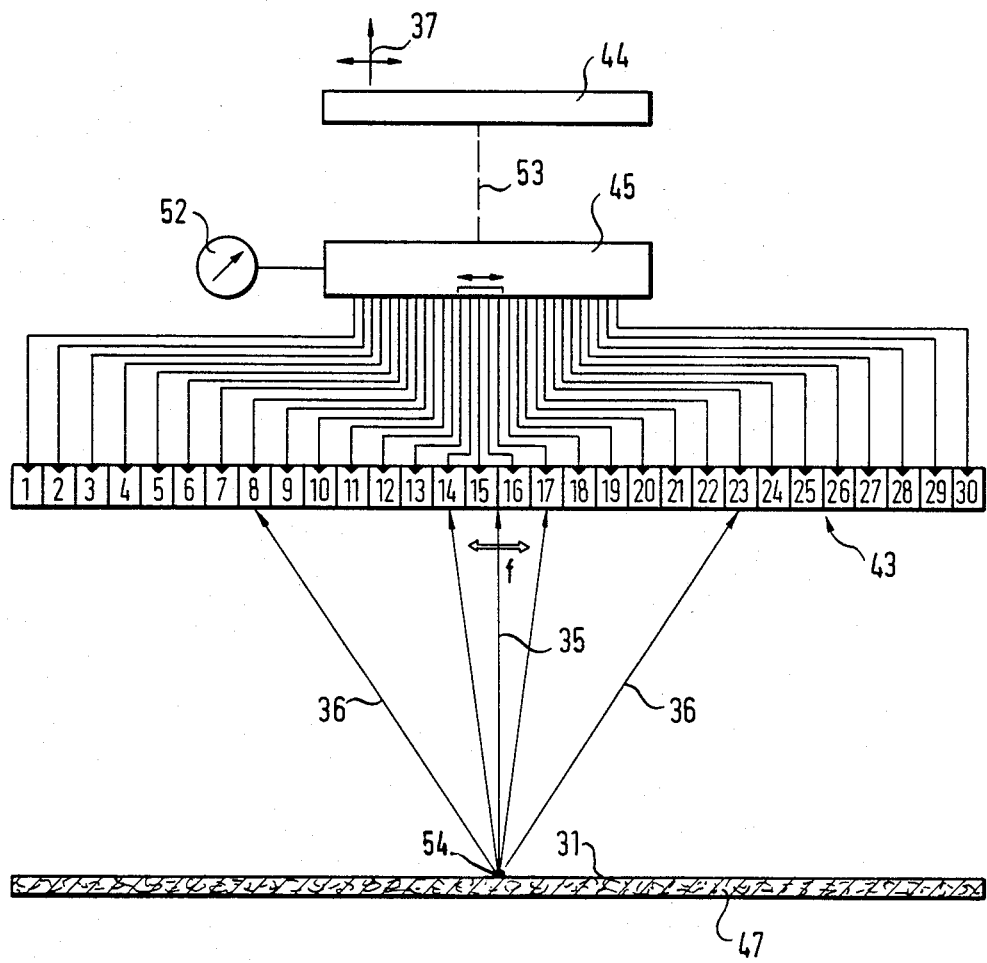

FAULT DETECTION APPARATUS FOR MATERIAL WEBS

This ia a division of application Ser. No. 235,694, filed Feb. 18, 1981, now U.S. Pat. No. 4,450,359.

The invention relates to a fault detection apparatus for material webs with a light transmitting device for generating a line of light on the material web and an elongate light receiving device which extends parallel to the line of light and is so arranged that it can receive light which enters a predetermined reception plane from the line of light, with the predetermined reception plane lying at a specified angle to the plane normal to the material web and containing the line of light.

The light used to illuminate the line preferably consists of coherent light of a quite specific frequency which is expediently generated by a laser. It will be appreciated that the line of light can be formed in different ways. It can for example be a continuous line of light generated by a light transmitting device in the form of an elongate light source. The light transmitting device can also advantageously transmit a sharply defined light beam which periodically scans the material web point by point line by line. In this arrangement the line of light is only illuminated at sequential points during the scanning movement.

When investigating the surfaces of band-like material using the beam scanning method a laser beam is guided over the surface in such a way that it scans the surface point by point line by line preferably with a constant angle of incidence. Depending on the structure of the surface a cone of scattered light is created with a preferential direction which lies at the characteristic angle of reflection. Individual faults in the surface lead to increased scattering. Information about surface faults is thus principally contained in those angular ranges of the scattered light which lie significantly outside of the angle of reflection. As the scattered cones are three-dimensional one has to distinguish, for the purpose of angular discrimination, between receiving devices which can filter out angular ranges within a plane extending at right angles to the line of light and receiving devices which respond to angular ranges within a reception plane which contains the line of light. Preferred reception planes are, for reflecting web material, the reception plane which lies at the angle of reflection to the plane of light incidence and, for translucent material, the reception plane which practically coincides with the plane of light incidence.

In order to be able to distinguish between different angular ranges in the plane which extends at right angles to the line of light it is already known to arrange light receiving devices having several light conducting rods arranged parallel to one another, in parallel in various reception planes (for example German patent publication DE-AS 24 33 682).

Difficulties arise however when it is necessary to discriminate between the angles of light beams which extend at different angles within a reception plane. The classical light conducting rod, which has an inlet side surface which is arranged to scatter light (German laying open print DE-OS 21 15 979), is not able to effect angular discrimination because incident light is scattered practically uniformly in all directions.

A light conducting rod with a prism like serrated light entry surface is also known (German patent publication DE-AS 19 41 905) in which the inlet prisms are inclined to the rod axis in such a way that a scanning light beam incident at right angles to the rod axis is refracted into the interior of the rod at angles of total reflection. This known light conducting rod however requires a transparent material with an unusually high refractive index. It does allow a certain degree of angular discrimination because side beams scattered at specific angles to the web surface are no longer refracted at angles of total reflection into the interior of the light conducting rod. For practical purposes however this light conducting rod is also not usable as a means for effecting angular discrimination because the very intense main beam is fully and completely deflected into the interior of the light conducting rod whereas the relatively weak side beams fail to reach the receiving device. Directly the reverse is necessary for successful fault recognition. In addition, receiving device are also known (German patent publications DE-AS 25 32 603, DE-AS 27 27 927) for detecting light beams which leave a web surface at different angles within a reception plane. These receiving devices operate with a stepped mirror arrangement in a surface zone of a light conducting rod which lies diametrically opposite to the light inlet of the light conducting rod. In this way the different angles of reflection of the received light beams which enter the light conducting rod at different angles within the scanning plane are exploited in order to illuminate the photoelectric converter which is associated with the angular range under consideration. However, the known devices require light conducting rods and stepped mirror arrangements of very high optical quality in order that an angle of reflection assiciated with a specific side beam is maintained during all the reflections within the light conducting rod. The possibilities of angular discrimination are restricted for these known receiving devices by the unavoidable imperfections of the known light conducting rods.

Finally it is also known for the purpose of angular discrimination in the reception plane (German patent publication DE-AS 28 00 351) to arrange, at the centre of a light conducting rod, a deflecting mirror which stops out the main reflection beam and deflects this to a special photoreceiver. This known arrangement however requires a high grade, bulky and heavy concave mirror which extends over the whole width of the web.

The object of the present invention is thus to provide an apparatus of the initially named kind which, in similar fashion to a light conducting rod, can uniformly pick up scattered light from the whole scanning range of the scanning light beam, but which nevertheless, for each scanning point, brings about discrimination of the scattering angle within a reception plane containing the line of light and indeed either in such a way that beams around the angle of specular reflection are either not received or received with a relatively low intensity when compared with beams the scattering angles of which within the reception plane exceed a specified minimum value, or in such a way that preferred bundles of rays with predetermined central scattering angles are detected. It is also of interest in individual cases to preferentially detect just a small angular range around the angle of specular reflection.

To solve this problem the invention envisages that an elongate angular range filter is arranged between the line of light and the light receiving device parallel to the light receiving device with said angular range filter not allowing received light beams lying within a predetermined angular range in said reception plane to reach the light receiving device but only received light beams lying outside this angular range.

The construction is usefully such that the angular range filter allows received light beams lying in a predetermined angular range in the reception plane and containing the largest part of the light leaving fault free areas of the web to pass the light receiving device or, alternatively, absorbs these received light beams but allows deflected light beams which lie outside of this angular range, and which have been deflected by faults out of the normal direction within the reception plane, to reach the light receiving device.

In principle either the received light beams lying outside of the predetermined angular range, or within this angular range, can be deflected whereas the remainder of the received light beams can be transmitted. It is however preferred for the received light beams lying within a predetermined angular range in the reception plane to be deflected and for the received light beams which lie outside of this angular range to be transmitted without hinderance. Alternatively, the components with undesired angles can be absorbed in the apparatus.

For preference, not only the received light beams which lie outside of the predetermined angular range but also the received light beams which lie within the predetermined angular range are passed to a further elongate light receiving device.

Inasmuch as the detection of faults in the material web is effected using light which falls obliquely on and is reflected from the surface of the web, the reception plane should be arranged at the angle of reflection to the plane of incidence of the light. If, for a light transmitting web, one is operating with transmitted light then the reception plane practically coincides with the plane of incidence of the light apart that is from any beam displacements which occur. These solutions are particularly advantageous because the light beam which has been reflected at the angle of reflection at fault free positions of the web surface, or transmitted undisturbed, and which contains the largest fraction of the total light intensity, is kept completely remote from the light receiving device so that "cross talk" into other angular ranges which can never be completely avoided as a result of scattering or refractive effects, is precluded. For those known scanning devices where the main light beams can admittedly be separated from the side beams at the receiver, the entry of the strong main light beams into the light conducting rod also results in the converters which are intended to receive the side light beams which are incident at a larger angle being illuminated as a result of scattering at dust or inhomogeneities of the light conducting rod. In accordance with the invention these very intense, main light beams around the angle of specular reflection, or the angle of transmission, are completely filtered out before they can enter into the light receiving device. They can therefore no longer disturb the sensitive measurement of the side beams which extend at larger scattering angles and which pass through the angular range filter.

It is particularly preferred for the invention to be used with a fault detecting apparatus in which the line of light is generated by light beams which occur at right angles in the plane of incidence of the light, in particular by a scanning beam which is generated by a light scanning device and which is displaced parallel to itself. In this case the angular range filter of the invention should have constant filter characteristics over its whole length so that a uniform fault indication is ensured along the whole scanned length.

A particular advantage of the invention resides however in the fact that it can also be used with fault detection apparatus of the kind in which the light beam is generated by light beams which lie in the plane of incidence of the light but are incident at different points and at different angles, in particular by a scanning beam from a light scanning device which executes a sector-like scanning movement. For this kind of fault detection apparatus the filter characteristics of the angular range filter expediently change along its length in accordance with the changing angle of incidence of the light beams along the line of light. The filter characteristics are however once again constant relative to the direction of incidence of the received beam on the individual points of the angular range filter. This embodiment is particularly preferred because a sector-like scanning beam can be generated without using an expensive and space consuming strip-like concave mirror, for example solely by using a mirror wheel. On the other hand the cost and complexity of manufacturing an angular range filter with filter characteristics which vary along its length are very small so that on the whole this embodiment leads to a considerable saving. Only the light receiving device need to be longer than for the case of a scanning beam which is displaced parallel to itself in order to take into account the oblique incidence of the side light beams.

A useful further modification of the invention is characterized in that differently constructed angular range filters are arranged in two directly neighbouring reception planes with separate light receiving devices being associated with each angular range filter. Each of the two angular range filters is tuned to different angular ranges and this makes it possible to filter out an individual, desired angular range. An arrangement of this kind, which can be made even finer by division into further angular range filters, thus makes it possible to perfect further the recognition of faults.

A particularly effective angular discrimination is possible when the angular range filter is an interference grating preferably in the form of a volume hologram. This embodiment can be manufactured economically.

For classical gratings the light is deflected into several orders. In accordance with the invention however only those gratings are used in which a single order occurs as a result of a sinusoidal variation of the transmissivity, or of the reflectivity, or of the refractive index. By appropriate choice of the thickness of the grating the deflected light can be concentrated in one of the orders on both sides of the axis of symmetry. A sinusoidal variation of the darkness of the grating, of the gratings reflection characteristics, or of the gratings refractive index is automatically achieved if, during the recording of a hologram, the intensities of the object wave and the reference wave are selected so that the range of illumination lies in the linear part of the characteristic line for the photographic material. In order to avoid the effects of small influences of the non-linearity of the photographic material one can select the angle of diffraction so that even the second order of the diffracted light can no longer propagate in the material. The theoretical angle of deflection of the second order must thus be greater than 90° relative to the normal to the surface of the diffraction grating.

An interferometer consisting of a few and at least two reflecting surfaces at a predetermined separation from one another can also be considered as an angular range filter. An example of an interferometer of this kind is the Fabry-Perrot interferometer which consists of two mirrors with a small spacing therebetween. In an interferometer of this kind the transmissivity varies with angle for a given wavelength of light. It will be understood that when using an interference grating as an angular range filter it is necessary to operate with monochromatic light which is matched to the grating constant of the grating.

The size of the angular range around the light beams which are deflected by the inference grating and thus directed past the light receiving device or to a light receiving device, can be adjusted by selecting the thickness of the hologram (the Bragg condition) and by choosing the wave form during the recording of the hologram. It is particularly advantageous if the light beams deflected at the hologram within a specific angular range about the angle of specular reflection are passed to a special observation device which can for example likewise contain a light conducting rod. The main light beam can in this way also be measured, for example with regard to its intensity. If desired the hologram can also be so arranged that it only deflects light beams with larger scattering angles or light beams within one or other predetermined angular scattering range.

The manufacture of the intereference grating of the invention preferably takes place by forming the hologram on a light sensitive material by a reference wave corresponding to light leaving the line of light at the angle of interest and by an object wave incident at the desired angle of deflection thereto.

The use of a hologram as the angular range filter also makes it possible, in simple manner, to realize a further embodiment in which several holograms are superimposed in the interference grating independently of one another so that several angular ranges can be simultaneously deflected to several spatially separated detectors. Moreover, it can also be advantageously arranged, by superimposing spherical waves when recording the hologram, that the hologram simultaneously has a gathering effect.

In addition the angular range filter can, in accordance with the invention be a grid of thin plates with the thin plates being constructed to be light absorbing on at least one side. The desired angular scattering ranges can be accurately filtered out of the light reflected from the material web by appropriate selection of the spacing of the thin plates, the length of the thin plates and also the angle of the thin plates. Instead of grids of thin plates it is also possible to select other directionally selective arrangements which operate by geometrical shading in an equivalent manner. Such directionally selective arrangements can for example consist of tubes, cones or grid-like structures arranged at a predetermining spacing in two planes. It is important in each case that the arrangement of the two planes is selected so that the light beams in a predetermine angular range cannot pass through the arrangement.

All shade producing geometrical arrangements have the common characteristic that approximately one half of the incident light in the desired solid angle range is lost by absorption. This is in general without practical significance. The transmission range of thin plate-like structures can however be enlarged by making the thin plates absorbent on one side and reflective on the reverse side.

All structures of this kind generate a certain periodic modulation of the light flux during the scanning procedure. The strength of this modulation depends on the spacing of the thin plates and their spacing from the scattering plane. This modulation is in general negligible if the spacing of the thin plates is very small relative to the spacing from the scattering plane. As an example a spacing between the thin plates of 1 cm as compared with a spacing of 20 cm from the scattering plane has been found to be useful in practice.

A further advantageous embodiment is so constructed that the angular range filter consists of an arrangement for selecting specified states of polarization. In this connection the scanning light beam should be preferably linearly polarized and a crossed analyser should be arranged in the path of the received beam. The transmitted light is preferably polarized at right angles to the plane of the scanning beam. In this respect the invention makes use of the recognition that the state of polarization of polarized light changes on reflection at a scattering medium and that this change generally becomes larger as the deviation of the scattering angle from the angle of the direct specular reflection increases.

Thus, in accordance with the invention, the specularly reflected very intense main light beam from the analyser is practically not transmitted. The more strongly the light beams are scattered relative to the main reflection beam the greater is the change in their state of polarization, i.e. they are more readily transmitted by the analyser. The consequence is again that only scattered light components which originate from faults can reach the light receiving device.

In accordance with the invention the various angular range filters can also be combined with one another to optimize the desired effects. It is particularly advantageous if a grid of thin plates is inserted in the beam path of the non-deflected scattered beams after an angular range filter in the form of a hologram. Because the holographic angular range filter has the property that a certain residual percentage of the light intensity of the light beams that are to be deflected pass through the filter it is expedient to filter out these transmitted light components by the grid of thin plates which is inserted in front of the light receiving device.

The elongate light receiving device is in all embodiments preferably a light conducting device, with, if required, a cylindrical lens inserted before the light conducting device which, by modulation of the beam direction collects all incident light beams onto a detector which is small in size relative to the longitudinal dimension of the light receiving device. It is particularly advantageous for the light conducting arrangement to be a light conducting rod which carries a stepped mirror arrangement at its side surface diametrically opposite to the light inlet, with the stepped mirror arrangement deflecting all incident light beams at angles of total reflection into the light conducting rod and with a photosensitive detector located at at least one end face of the light conducting rod. In this embodiment the angular range filter should preferably be arranged between the cylindrical lens and the light conducting device because space which is not otherwise required is generally available at this location.

A further solution of the problem underlying the invention is based on fault detection apparatus for material webs with a light transmitting device for generating a line of light on the material web and an elongate light receiving device which extends parallel to the line of light and is so arranged that it can receive light which enters a predetermined reception plane from the line of light with the predetermined reception plane lying at a specified angle to the plane normal to the material web and containing the line of light, with the light receiving device comprising a light conducting rod with a stepped prism arrangement at its surface diametrically opposite to the light inlet and at least one photoelectric converter at at least one end face. With this arrangement the invention envisages that the stepped prism arrangement is unmirrored and that the inclination of the individual prism surfaces is so selected that received light beams extending in a predetermined angular range in the reception plane are transmitted whereas received light beams extending outside of this angular range are incident on the prism surfaces at angles of total reflection and are reflected into the interior of the rod.

The angular ranges lying around the main specularly reflected beam are thus transmitted by the light conducting rod and can preferably be detected separately in a receiver inserted after the light conducted rod, with this receiver also preferably containing a light conducting rod. To avoid disturbing dielectric reflections in the transmitted angular ranges it is advantageous to demirror the prism surfaces for the central angle of incidence of the angular range which is to be transmitted.

Finally a third solution envisages that the light receiving device consists of a number of light receivers which can be selectively switched in with at least one of the light receivers being switched out at each particular instant. The practical embodiment is preferably such that the light receivers are cyclically switched out either individually or in groups by an electronic switching device with the switching device being controlled by the scanning device for generating the scanning light beam in such a way that received light beams extending within a predetermined angular range in the reception plane fall on light receivers which are at that instant switched out whereas only light beams extending outside of this angular range fall on light receivers which are switched in.

The light receivers used in this arrangement can either be straightforward photoelectric converters or, for example, can also be short light conducting rods arranged one behind the other. By selecting an appropriate length of the light receiver in the scanning direction, or by connecting together one or more light receivers to form simultaneously switched groups, the angular ranges within the reception plane which are stopped out during reception can be readily specified.

Figure 2:
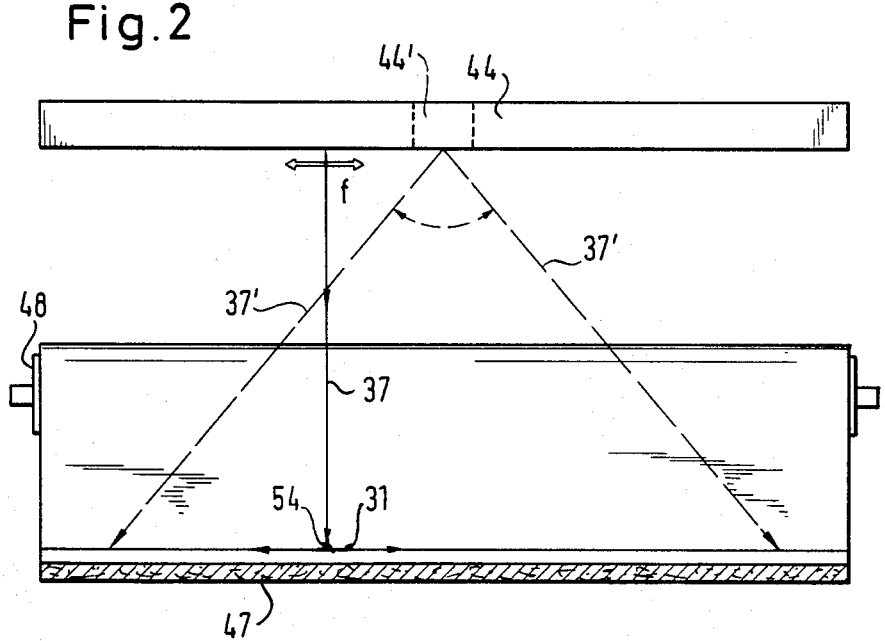
Figure 1A:
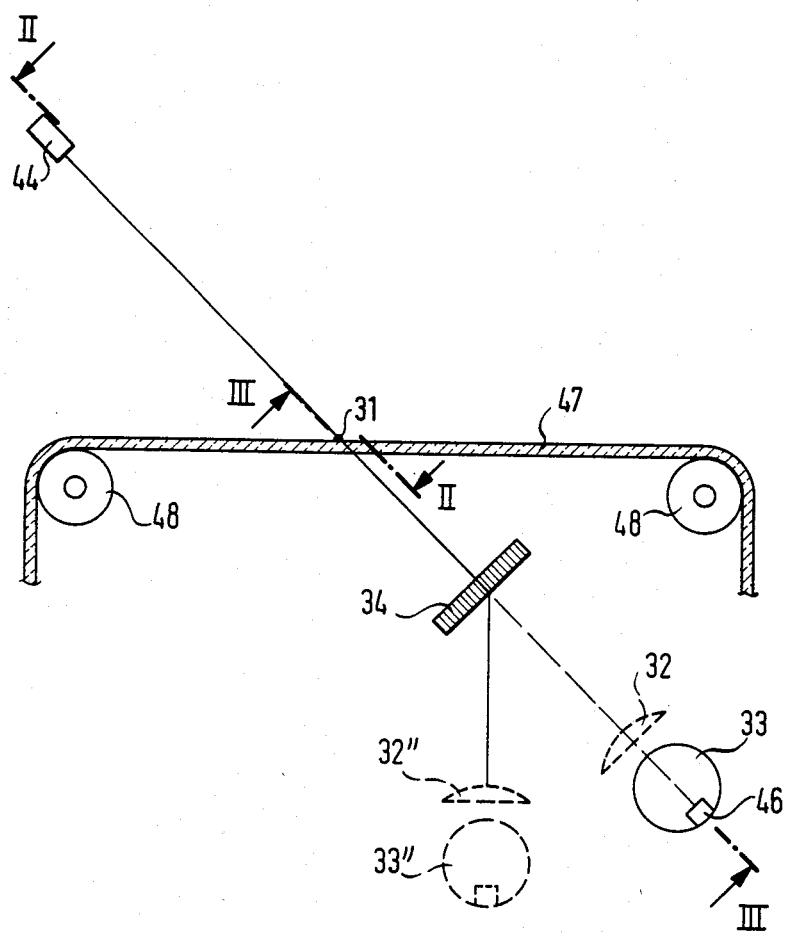
Figure 1B:
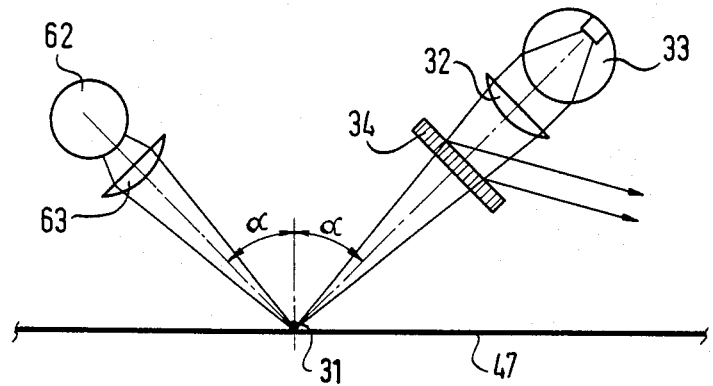
Figure 1C:
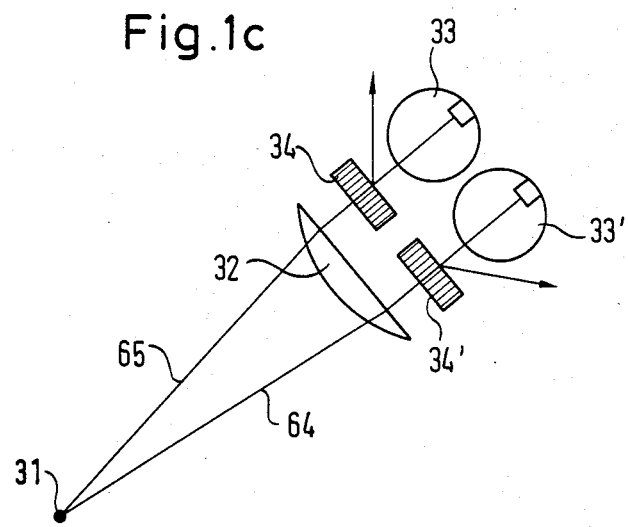
Figure 3:
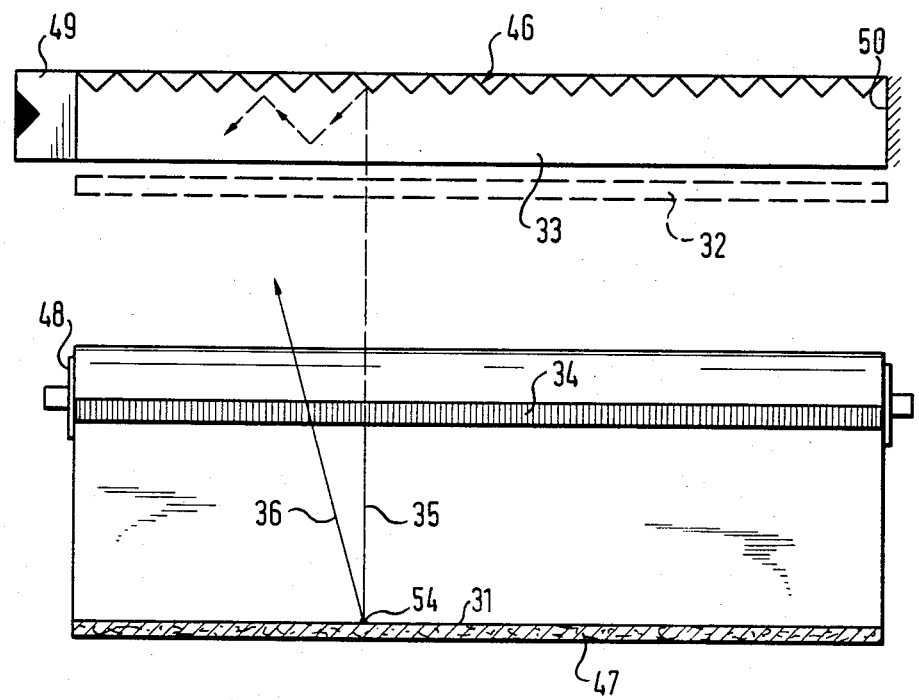
Figure 3A:
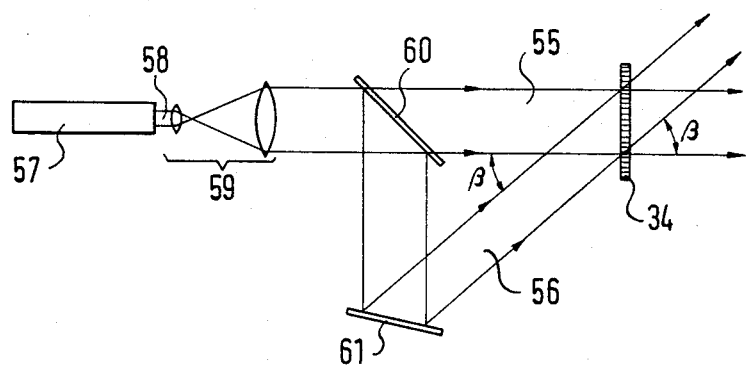
Figure 3B:
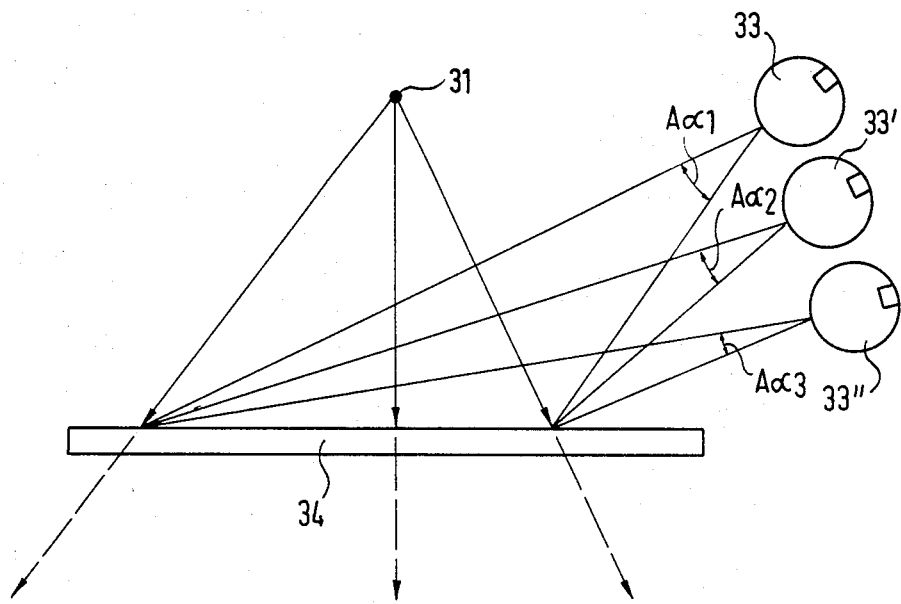
Figure 4:
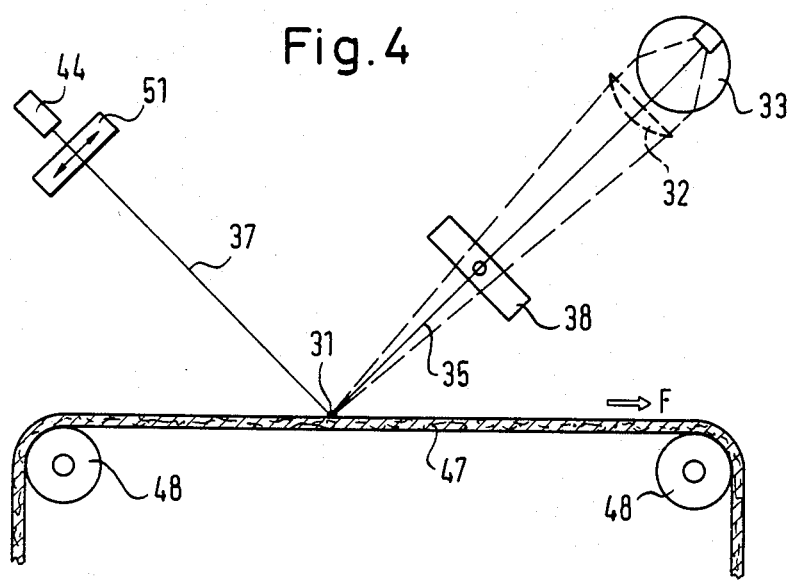
Figure 5:
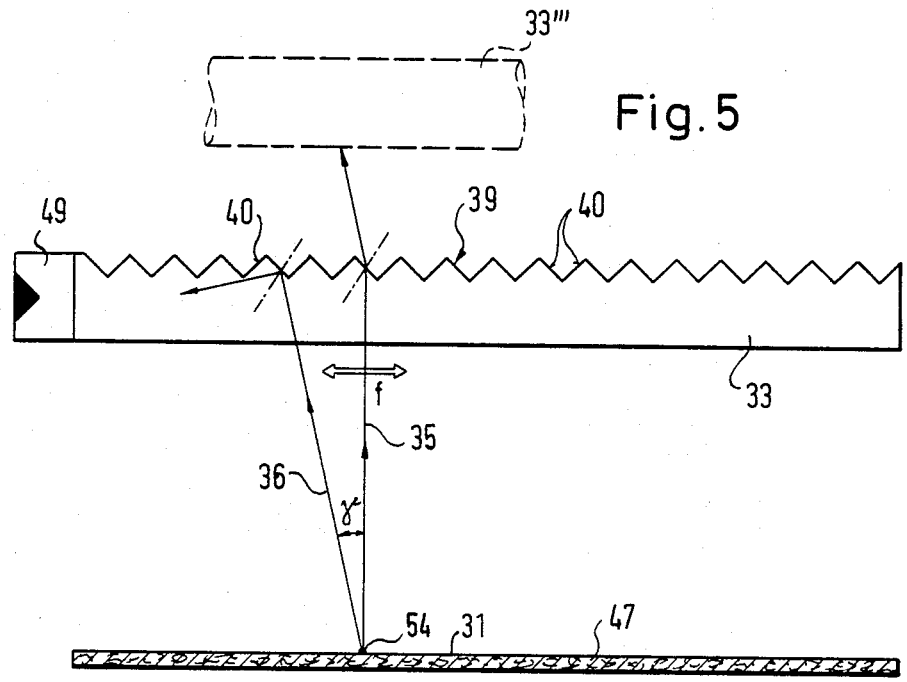
Figure 6:
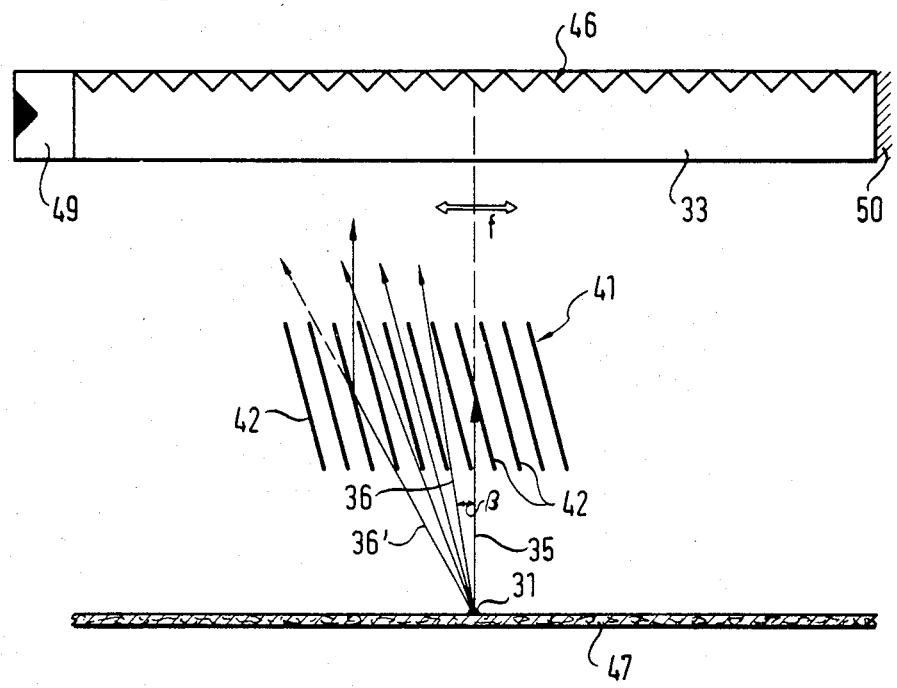
Figure 7:
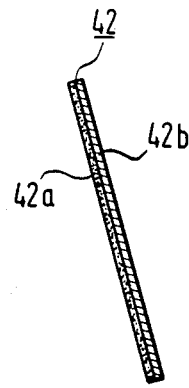
Figure 6A:
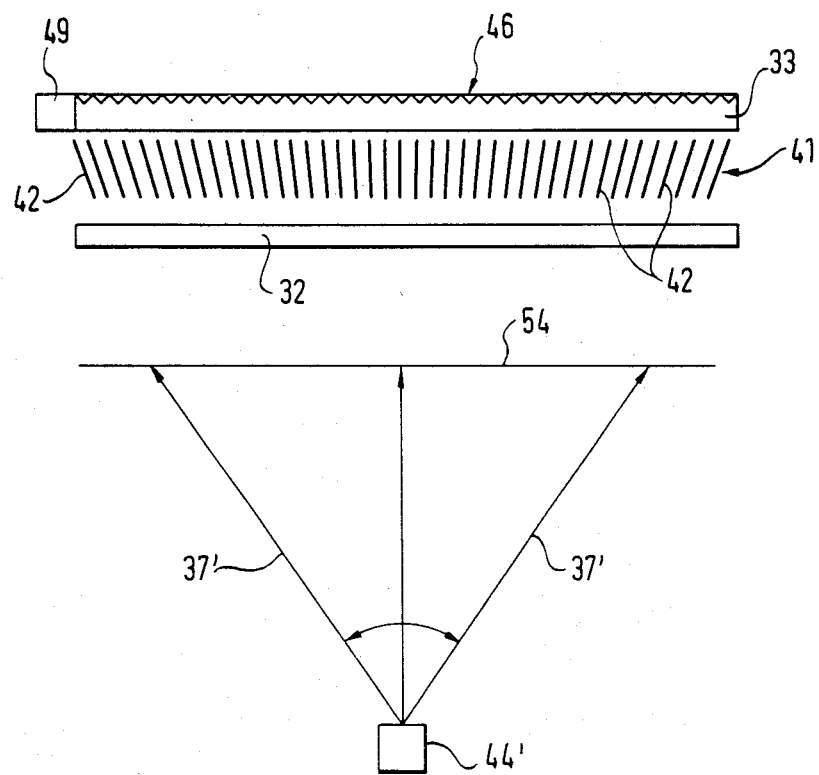

The invention will now be described in the following by way of example and with reference to the drawings which show:

FIG. 1 a schematic side view of a fault detection apparatus in accordance with the invention which operates in reflection using a hologram with the view being taken in a plane at right angles to the direction of scanning f, FIG. 1a a view similar to that of FIG. 1 showing a fault detection apparatus used in conjunction with a light transmitting web and operating in transmitted light, FIG. 1b an embodiment which, in contrast to the preceding embodiments, operates with a continuous line of light, FIG. 1c an embodiment which operates with two angular range filters arranged in parallel, FIG. 2 a view on the line II—II of FIGS. 1 and 1a to define the plane of the scanning beam, FIG. 3 a section on the line III—III of FIGS. 1 and 1a to define the scanning plane, FIG. 3a a preferred beam path for producing a hologram which can be used as an angular range filter in accordance with the invention, FIG. 3b an embodiment with a hologram which is simultaneously tuned to various angular ranges, FIG. 4 a view analogous to that of FIG. 1 of an embodiment operating with polarization filters, FIG. 5 a view analogous to that of FIG. 3 of a further embodiment which operates with a light conducting rod having an unmirrored stepped prism arrangement, FIG. 6 a view analogous to that of FIG. 3 of a further embodiment which operates with a grid of thin plates, FIG. 6a an embodiment analogous to that of FIG. 6 with a grid of thin plates which has different filter characteristics along its length in order to cooperate with a sector-like scanning beam, FIG. 7 an enlarged end view of one of the thin plates of the grid of thin plates used with the embodiment of FIG. 6 and FIG. 8 a view analogous to that of FIG. 3 showing an embodiment of the detection apparatus of the invention which operates with cyclically switched light receivers.

As seen in FIGS. 1 to 3 a scanning light beam generating device 44 generates a sharply defined, monofrequency, coherent, laser light scanning beam 37 which executes a periodic to and fro movement parallel to itself in the direction of the double arrow f in the scanning beam plane of FIG. 2. The scanning light beam generating device 44 contains, by way of example, a laser as the light source, a mirror wheel which produces the scanning movement and a concave mirror which makes the scanning light beams parallel. A scanning light beam generating device suitable for the purpose of the invention is, by way of example, described in German laying open print DE-OS 24 33 682.

As seen in FIG. 1 the generating device 44 for the scanning light beam is so arranged that the scanning light beam 37 falls at an angle α on a material web 47 and there forms a scanning light bead 31 which generates, for scanning purposes, a line of light 54 as a result of its to and fro movement. The material web 47 is led past the point of incidence of the scanning light beam 37 around two deflection rollers 48 in such a way that the direction of movement F of the web extends at right angles to the scanning direction f. The speed of advance of the web 37 and the period of the scanning light beam 37 are so selected that as the web 47 advances it is scanned line by line the scanning light bead 31 which is generated on the surface of the web 47 by the scanning light beam 47.

The main light flux of the scanning light beam 37 is reflected in a direction towards a light receiving device 32, 33 at an emergent angle α which is equal to the angle of incidence α. The specular main reflection beam is illustrated by a solid line in FIG. 1. As a result of a greater or lesser degree of scattering at the surface of the web 47 light is however also reflected from the web at angles which deviate from the main angle of reflection α. This is indicated by broken lines in FIG. 1.

Without the hologram 34 which is illustrated in FIG. 1 the received light would be deflected in the manner illustrated in broken lines in FIG. 1 via a cylindrical lens 32 into a light conducting rod 33 of round cross-section where it would then be concentrated on a stepped mirror arrangement 46 which can be seen in detail from FIGS. 1 and 3. The cylindrical lens 32 and the light conducting rod 33 are arranged with their axes parallel to the scanning direction f. As indicated in broken lines in FIG. 3 the received light would be reflected at the individual mirrors of the stepped mirror arrangement 46 into the interior of the rod at angles such that the light of the main reflection beam 35 would reach a photoelectric converter 49 arranged at at least one end face of the light conducting rod 33 as a result of total reflection at the walls of the light conducting rod 33. A photoelectric converter can also be likewise arranged at the opposite end face. A mirror surface 50 is however preferably provided at the other end face so that light incident on the mirror surface is reflected back into the light conducting rod 33 so that it eventually likewise reaches the photoelectric converter 49.

It is important that the cylindrical lens 32 and the round form of the light conducting rod 33 result in the received light converging on the stepped mirror arrangement 46 in the view of FIG. 1 so that, after a further reflection at the inner wall of the light conducting rod 33, the light reflected from the stepped mirror arrangement 46 does not once again fall on the stepped mirror arrangement 46 which should be of relatively narrow construction.

Whereas light scattered at angles significantly greater than the main angle of specular reflection as a result of faults in the surface of the web 47 could be captured by one or more further light receiving devices, of which one is indicated by way of example at 33', it would normally not be possible to achieve angular discrimination in the reception plane of FIG. 3 between the main angles of specular reflection and the angles of scattering. In order, however, to achieve angular discrimination of this kind in the plane of FIG. 3 a hologram 34 is arranged, in accordance with the invention, between the scanning light bead 31 and the light receiving device 32. The hologram 34 is so constructed that it deflects the main specularly reflected light beam 35 together with a narrow angular range about this light beam sufficiently far sideways in the plane of FIG. 1 that this light passes by the main light receiving device 32, 33. This light can one, if desired, be captured by a further light receiving device consisting of a cylindrical lens 32" and a light conducting rod 33". As a result of this construction the main reception light beam 35 which is reflected at the angle of specular reflection no longer reaches the main light receiving device 32, 33. In contrast received light beams which are reflected from the web 47 in the plane of FIG. 3 at an angle above a predetermined scattering angle reach the light conducting rod 33 through the hologram 34, substantially without hinderance, and are deflected by the stepped mirror arrangement 46 to the photoelectric converter 49. Thus, in accordance with the invention, the received bundle of light rays around the specularly reflected main light beam which contain the principal light intensity are deflected past the light conducting rod 33 of the light receiving device.

The hologram 34 is formed in accordance with the invention by the superposition of a plane wave which propagates in the scanning beam plane (FIG. 2) and a plane wave in the direction of the beam 35 in FIG. 1. The angular range deflected by the hologram is determined by the thickness of the hologram in accordance with the Bragg condition. This angular range can be influenced by using a wave of finite aperture as a reference beam for the manufacture of the hologram.

The manufacture of a hologram which is suitable for the scanning apparatus of FIGS. 1 to 3 will be described in detail in the following with reference to FIG. 3a:

The sharply defined beam 58 delivered from a laser 57 is widened by a lens system 59 in the manner which can be seen from FIG. 3a and is divided by a beam divider 60 into two part beams. The plane wave which simply passes through the beam divider 60 is designated a reference wave 55. The reference wave falls perpendicularly on a light sensitive material which will later form the hologram 34. The light beam which is deflected at the beam divider 60 is reflected at a deflecting mirror 61 and forms an object wave 56 which intersects the reference wave 55 at an angle $\beta$. The light sensitive material which later forms the hologram 34 is positioned, in the manner which can be seen from FIG. 3a, in the plane of intersection of the reference wave 55 and the object wave 56. A stationary interference field, which is recorded on the photosensitive material, is present in the zone of intersection of the reference wave 55 and the object wave 56. After developing the latent interference image a hologram is then present which, on illumination with the reference wave 55 alone converts the reference wave into the object wave 56 This corresponds to a deflection of the reference wave 55 through the angle $\beta$ on passage through the hologram 34.

On using the hologram 34 within the context of the present invention the reference wave 55 corresponds to the wave coming from the line of light 54 inside the predetermined angular range. The deflected beam then corresponds to the object wave 56 (FIG. 1).

If one were to use a spherical wave as the reference wave 55 then the hologram would not only deflect light at the angle of reflection but also a larger angular range.

Whereas in FIG. 1 an arrangement is shown which operates in reflection at the angle of reflection FIG. 1a illustrates the application of the invention to a fault detection apparatus which operates with transmitted light. The main light beam is deflected by the hologram 34 whereas the light which is scattered, for example at optical inhomogeneities in a transparent foil 47, reaches the light receiving device 32, 33 without hinderance.

FIG. 1b shows how the line of light 54 can also be generated by arranging a fluorescent tube 62 parallel to the web 47 using a cylindrical lens 63 which extends parallel to the fluorescent tube 62 to concentrate the band of light onto the line 54. The possibility of using a continuous line of light 54 in place of a scanning light beam is a particular advantage of the invention because one can avoid movable deflecting elements. All the light which is normally reflected from the web 47 is namely deflected past the light receiving device 32, 33 by the hologram 34. Only light which is scattered in the reception plane at some kind of fault reaches the light receiving device 32, 33.

FIG. 1c shows how light received from the line of light and extending in two reception planes 64, 65 which lie close to one another can be divided by a cylindrical lens 32 between two angular range filters, in particular holograms 34, 34' which are arranged alongside one another with an individual light receiving device, in the form of light conducting rods 33 and 33", being associated with each of the angular range filters 34 and 34' respectively. The angular range filters 34, 34' are expediently so constructed that they deflect different angular ranges within the reception planes 64 and 65 as is illustrated by arrows. Only the scattered components which lie outside of these deflected angular ranges and within the planes 64, 65 reach the light conducting rod 33 and 33' respectively.

FIG. 3b shows a multiple angular range filter 34 which can be formed by a thick hologram. For this purpose several different interference fields are recorded in the light sensitive material which is used to manufacture the hologram. The filter can in this fashion simultaneously deflect several different angular ranges to several spatially separated light receiving devices 33, 33', 33" respectively. The hologram 34 can also be simultaneously endowed with a gathering effect by superimposing cylindrical waves during the recording. The hologram has the property that, even at restricted efficiencies, the deflected beam fractions are almost free from undesired angular components. All the angular components are once again present in the transmitted part of the light.

FIG. 4 shows a view analogous to that of FIG. 1 with the same reference numerals designating parts which correspond to parts illustrated in FIG. 1. In distinction to the embodiment of FIG. 1 the scanning light beam 37 extends through a linear polarizer 51, the direction of polarization of which lies in the plane of FIG. 4, before falling on the web 47. The light reflected from the scanning light bead 31 substantially in the direction of the light receiving device 32, 33 is accordingly likewise linearly polarized. The main received beam 35 together with a certain angular range around the main reflection beam 34 can thus be kept away from the light receiving device 32, 33 by a crossed analyser 38 arranged between the scanning light bead 31 and the receiving device 32, 33. The side beams which are more strongly scattered in the detection plane are however more or less depolarized so that they pass through the analyser 38 to a greater or lesser degree and can be detected by the receiving device 32, 33. An electrical signal characteristic of the intensity of the side beams is thus created at the photoelectric converter 49 and can be used for evaluating faults.

The embodiment of FIG. 5 operates with a special light conducting rod 33 as a receiver for light beams which are reflected from the web 47. A stepped prism arrangement 39 is provided on the side surface which lies diametrically opposite to the light inlet and consists of individual roof or sawtooth-like plane prism surfaces 40 which are arranged in a row. The inclination of these prism surfaces 40 relative to the axis of the light conducting rod 33 is important for the invention. As is illustrated, using the example of the main reflection beam 35 and a side beam 36 which is reflected at a certain scattering angle $\gamma$ relative to the main reflection light beam, the inclination of the prism surfaces 40 is so selected that the main reflection light beam 35 including beams inside a narrow angular range around the main reflection light beam are not totally reflected following incidence on the prism surfaces 40 but instead emerge through the surface where they can be captured by a secondary light conducting rod 33''' and used to generate a signal. Above a certain limiting angle in the light conducting rod 33 light beams which enter in the plane of FIG. 5 fall on the plane prism surfaces 40 at angles of total reflection so that, as shown for the example of the received beam 36, the received light is reflected into the interior of the light conducting rod 33 where it eventually reaches the photoelectric converter 49 after multiple reflection at the walls of the light conducting rod 33.

The relatively weak scattered light beams 36 can thus be detected for measurement purposes by the converter 49 without significant interference by the main beams 35.

Using this arrangement one half of the scattered and totally reflected light is however lost because this light falls on the stepped prism arrangement at an angle less than the limiting angle for total reflection. This is however not significant with regard to the contrast increasing effect of the arrangement.

In the embodiment of FIG. 6 the light conducting rod 33 once again corresponds to the light conducting rod shown in FIGS. 1 to 3, the arbitary cylindrical lens 32 has however not been shown so as to simplify the illustration.

As seen in FIG. 6 a grid 41 of thin plates 41 is arranged between the scanning light bead 31 and the light conducting rod 33 of the light receiving device with the thin plates 42 being disposed in an inclined position however parallel to one another. The spacing, length and angle of the thin plates 42 are so selected that the specularly reflected main light beam 35 and received light beams lying in a specified angular range around this main light beam cannot pass the grid 41 because the spacing, angle and length of the thin plates 42 are approximately selected, by way of example, in accordance with the dimensions of FIG. 6. The impingement side of the thin plates 42 is provided with a light absorbing layer 42a as shown in FIG. 7.

Received light beams 36 which are scattered at angles greater than the main light beam 35 can however pass through the space between the thin plates 42 to the light conducting rod 33 of the receiving device. The presence of the beams 36 is indicated following reflection at the stepped mirror arrangement 46 and reception by the photoelectric converter 49.

The rear sides of the thin plates is preferably provided with a specularly reflecting coating 42b as shown in FIG. 7 so that received beams 36' which are incident at very large scattering angles (FIG. 6) are likewise still deflected to the light conducting rod 33. The transmission range of the grid 41 of thin plates is substantially enlarged in this manner.

In order to avoid a concave mirror which takes up a lot of space it is possible to use a scanning light beam 37' which executes a sector-like scanning movement by making use of a suitable light beam generating device 44' as shown in FIGS. 2 and 6a. This scanning light beam 37' however falls in the incident light plane (FIG. 6a) at angles to the scanned line 54 which are continuously changing so that the beam which is reflected from the web at the corresponding main angle of reflection also has a continuously changing angle in the reception plane. In order, in this case also, to ensure that the main reflection beams can be deflected without problem the grid 41 of thin plates is constructed, in accordance with FIG. 6a, in such a way that it has different filter characteristics along its length. The individual thin plates 42 are arranged at different inclinations to one another along the length of the grid so that the respectively occurring main reflection beam is always captured by the grid of thin plates in the same manner irrespective of the angle within the sectorlike scanning range. Thus, a substantially constant filter behaviour is achieved over the whole length of the grid 41 of thin plates despite the sector-like scanning range of the scanning light beam 37'.

The hologram 34 of the invention can also be constructed with different filter characteristics along its length, for example, by forming the reference wave as a spherical wave by the insertion of a lens when using the method of FIG. 3a. A hologram 34 can thus be manufactured which ensures a constant deflection behaviour over the whole length of the hologram 34 despite the use of a sector-like scanning light beam 37′. Because a hologram has a specific efficiency, which can moreover reach 90%, the hologram will always transmit a part of the light flux which is intended to deflect. For this reason it is expedient, in accordance with FIG. 1, to combine a grid 41 of thin plates as shown in FIGS. 6 to 7 with a hologram 34 as shown in FIG. 1. For this purpose the grid 41 of thin plates can be arranged between the cylindrical lens 32 and the light conducting rod 33. The grid is constructed to allow the unhindered passage of the scattered radiation but to prevent the passage of the non-deflected main beam which arises as a result of the imperfections of the hologram 34.

As seen in FIG. 8 photoelectric converters 1 to 30 are arranged in a row alongside one another at the receiver side parallel to the direction of scanning 31. The photoelectric converters are respectively connected via a respective line to an electronic circuit device 45 which can for example have a fault display instrument 52 at its output. The photoelectric converters 1 to 30 together form an elongate light receiving device 43 the length of which corresponds to the length of the scanned line on the surface of the web 47. As seen in FIG. 8, on the assumption that the light bead 31 is in the illustrated position, the main specularly reflected beam 35 and the closely neighbouring side beams fall on the inner photoelectric converters 14 to 17. In contrast the received beams 36 which are scattered at considerable angles reach the photoelectric converters 1 to 13 and 18 to 30. One now ensures, by suitable control of the electronic circuit device 45 that the photoelectric converters 14, 15, 16 and 17 are switched off at the moment reproduced in FIG. 8. The electronic circuit device at 52 therefore only indicates the light which originates from the scattered light beams.

As however the main, specularly reflected, light beam 35 executes a periodic scanning movement in the sense of the double arrow f it is accordingly necessary to continuously switch off other photoelectric converters. This can take place by connecting the generating device 44 for the scanning light beam with the electronic circuit device 45 via a control line 53. The photoelectric converters present at the main angle of specular reflection can now be switched off in synchrony with the movement of the scanning light bead 31 so that the conditions reproduced in FIG. 8 for a specific instant are present throughout the whole scanning cycle of the scanning light bead 31. Greater, or smaller angular ranges around the main specularly reflected beam 35 can be excluded from the measurement by connecting more, or fewer, photoelectric converters into groups (in FIG. 8, 14, 15, 16 and 17 i.e. four photoelectric converters). Light conducting rods or the like arranged one behind the other can also be used as separate receivers in place of the photoelectric converters 31 to 33.

In the embodiment with a grid of thin plates as shown in FIGS. 6 to 7 the electrical output signal is modulated. The modulation can however be easily eliminated electronically by suitable filters.

The embodiment operating with a grid of thin plates also makes it possible, even for non-constant scanning speed of the scanning light beam, to obtain a constant modulation frequency simply by selecting different separations for the plates in accordance with the changing scanning speed along the scanning path so that a constant modulation frequency is obtained at the output of the photoelectric converter 49. This constant modulation frequency can, as already stated, easily be filtered from the output signal by a suitable filter.

We claim:

1. Fault detection apparatus for material webs comprising a light transmitting device for generating a line of light on the material web, said web having a width; and an elongate light receiving device extending parallel to the line of light and spaced therefrom to receive light scattered from said web in a reception plane containing said line and said elongate light receiving device, said light receiving device extending over at least said width of said web; wherein said light receiving device comprises a light conducting rod having a side surface and first and second end faces, an elongate light inlet extending along said side surface in said reception plane, a stepped prism arrangement in the form of a linear array of prism surfaces arranged along said side surface and disposed diametrically opposite to said light inlet, and at least one photoelectric converter at at least one of said end faces; and wherein said stepped prism arrangement is unmirrored and wherein the inclination of said prism surfaces is so selected that light beams which extend within a predetermined angular range with respect to said web in said reception plane and which enter said light inlet and fall on said stepped prism arrangement are transmitted through said stepped prism arrangement out of said rod, whereas received light beams extending outside of this angular range are incident on the prism surfaces at angles of total reflection and are reflected into the interior of said rod.

2. Apparatus in accordance with claim 1 and wherein the angle of inclination of said prism surfaces is such that a received beam lying in said reception plane within an angular range around the beam of light reflected from a fault free web is transmitted.

* * * * *